(12) United States Patent
Lövgren et al.

(10) Patent No.: US 7,192,786 B1
(45) Date of Patent: Mar. 20, 2007

(54) BIOSPECIFIC ASSAY METHOD

(75) Inventors: Timo Nils-Erik Lövgren, Kirjala (FI); Antti Juhana Iitiä, Masku (FI); Kim Sverker Immanuel Pettersson, Turku (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 08/487,623

(22) Filed: Jun. 7, 1995

Related U.S. Application Data

(63) Continuation of application No. 08/182,550, filed on Jan. 18, 1994, now abandoned.

(30) Foreign Application Priority Data

Mar. 16, 1993 (FI) .................................. 931151

(51) Int. Cl.
  *G01N 33/546* (2006.01)
  *G01N 33/54* (2006.01)
  *G01N 33/53* (2006.01)

(52) U.S. Cl. .................... 436/534; 435/6; 435/7.1; 435/7.5; 435/7.92; 435/7.95; 435/962; 435/968; 435/973; 436/518; 436/523; 436/531; 436/800; 436/814; 436/818; 436/825; 436/533

(58) Field of Classification Search .................. 435/6, 435/7.1, 7.5, 7.92–7.95, 962, 968, 973; 436/518, 436/523–531, 800, 814, 818, 825, 533, 534
See application file for complete search history.

(56) References Cited

U.S. PATENT DOCUMENTS 4,408,877 A * 10/1983 Lindmo et al. ............... 356/38
5,028,545 A * 7/1991 Soini ........................... 436/501
5,089,391 A * 2/1992 Buechler et al. ............. 435/7.1
5,516,635 A * 5/1996 Ekins et al. .................... 435/6

OTHER PUBLICATIONS

Bush et al., "Solid Phase Time-Resolved Fluorescence Detection of Human Immuno-deficiency Virus Polymerase Chain Reaction Amplification Products," ANAL. Biochem 202:146-151 (1992).*
Christopoulous et al., "Ultrasensitive Time-Resolved Fluorescence Method for α-Fetoprotein," Clin. Chem. 36:1497-1502 (1990).*
Ekins et al., "Multianalyte Microspot Immunoassay—Microanalytical Compact Disk of the Futute" Clin. Chem. 37:1955-1967 (1991).*
Frengen et al., "Homogeneous Immunofluorometric Assays of α-Fetoprotein with Macroporous Monosized Particles and Flow Cytometry," Clin. Chem. 39:2174-2181 (1993).*

* cited by examiner

*Primary Examiner*—Rodney P Swartz
(74) *Attorney, Agent, or Firm*—Kubovcik & Kubovcik

(57) ABSTRACT

This invention relates to a biospecific assay method, in which microparticles coated with the bioaffinity reactant A binding the analyte to be assayed; the sample to be analyzed, and the labelled bioaffinity reactant B are mixed. After the binding reaction the signal strength from the labelled bioaffinity reactant B bound to the microparticles is quantitated for the determination of the concentration of the analyte in the sample. According to the invention, such an amount of sample and microparticles is used in the assay that after binding of the analyte of the sample to the said amount of microparticles, each individual microparticle will emit such a signal strength as to allow the measurement of the analyte concentration over the whole range of typical analyte concentrations, and the signal strength from each microparticle is measured separately.

7 Claims, 2 Drawing Sheets

BIOSPECIFIC ASSAY METHOD

This is a continuation, of application Ser. No. 08/182,550 filed Jan. 18, 1994, now abandoned.

This invention relates to a biospecific assay method in which the analyte to be assayed is bound to the surface of microparticles through a bioaffinity reactant binding the aforesaid analyte, and the amount of analyte bound to individual microparticles is determined.

BACKGROUND OF THE INVENTION

The publications and other materials used herein to illuminate the background of the invention, and in particular, cases to provide additional details respecting the practice, are incorporated by reference.

Traditionally, radioimmunoassays were in the beginning performed in solution using test-tubes and complicated separation methods. With the advent of solid phase technology radioactive isotopes have been replaced by diverse labels, and especially monoclonal antibodies have been used in an increasing number of applications.

The aforementioned improvements have made a wider range of traditional immunoassays and other bioaffinity assay methods available (e.g. Alternative Immunoassays, W. P. Collins, Wiley, Chichester 1985, and Luminescence Immunoassay and Molecular Applications, Ed. Knox van Dyke, CRC Press, Boston 1990, and R. P. Ekins et al., Clin. Chem. 1991; 37:1955–1967). Solid phase assays have become routine assay methods both in the field of competitive and non-competitive assays, and the traditional test-tube has often been replaced by alternative solid phase facility. The microtiter plate was introduced as a solid phase for routine hormone assays in 1984 when Wallac Oy (Turku, Finland) introduced their DELFIA technology. Other commercial enterprises have also adopted the microtiter plate in similar routine assays, which, however, are based on different labelling technologies.

Microparticles manufactured of different materials have for some time been available as an alternative solid phase for bioaffinity assays (e.g. Molday W. J. et al., J. Cell. Biol.: 1975: 64, 75, and Nustad K. et al.: Microspheres. Medical and biological applications, Ed. A. Rembaum and Z. A. Tökes, Boca Raton, Fla., CRC Press 1988). Compared to microtiter plates the microparticles offer several advantages, for instance an immobilization method for bioaffinity reactants more easily adaptable to production scale, and a greater reaction velocity obtainable when using microparticles. The capacity of the microsphere-associated solid phase is also easily controllable by simply dispensing an amount of particles optimal for the method in question. The greatest disadvantages of microparticles have been traditionally associated with liquid handling (e.g. washes). With the introduction of magnetic microspheres this problem has been partly overcome, and in recent years an increasing number of commercial automated immunoassay methods have been based on their use. Nowadays novel manufacturing methods have allowed the production of microparticles of exact and reproducible size (e.g. of a diameter of 0.04–100 μm). Also the immobilization of the bioaffinity reactants onto the microparticles can be effected by various chemical methods.

The competitive biospecific assay method may be described as follows: The microparticles are coated with the bioaffinity reagent A, for whose binding sites, on the one hand, the analyte contained in the sample competes, and on the other hand, the bioaffinity reagent B, in this case an appropriately labelled analyte, also competes for the said binding sites. In the case of immunoassay, bioaffinity reagent B will be a labelled antigen, the antigen being the same as the antigen contained in the sample or to a suitable labelled derivative thereof. Because the analyte contained in the sample and the labelled analyte compete for the binding sites of the bioaffinity reactant A, the amount of label bound to the microparticle via reactant A, and consequently the signal from the microparticle, will be inversely related to the concentration of the analyte in the sample.

The non-competitive biospecific assay method may be described as follows: The microparticles are coated with the bioaffinity reactant A, whose binding sites only bind the analyte contained in the sample. The bioaffinity reactant B, which in this case is a suitably labelled reactant directed against the analyte contained in the sample, is bound by the analyte, which is linked to the microparticle via the bioaffinity reactant A. In the case of immunoassay, bioaffinity reactant B will be a labelled antibody directed against the antigen contained in the sample. The amount of label bound to the microparticle via reactant A, and consequently the signal strength from the microparticle, will be directly related to the concentration of the analyte in the sample.

The sensitivity of the competitive and non-competitive immunoassay has been extensively discussed earlier (Ekins R. P. et al., Pure and Appl. Chem., 1985; 57: 473–482, and Ekins R. P. et al., Clin. Chem., 1991; 37: 1955–1967). As regards the present invention, it is essential to consider the factors affecting the sensitivity and functionality of each assay principle.

Maximal sensitivity in a competitive immunoassay when using an antibody (a bioaffinity reactant) with an affinity constant K will be obtained by dividing by K the relative error of the signal strength at zero concentration. The error of the signal strength will be affected by two components, an experimental error component due to pipetting and other manipulations, and a signal strength measurement component, e.g. the statistical error of signal strength measurement. For the sake of simplicity, let us assume that the error due to signal strength measurement is 0, which is usually the case when the specific activity of the label is high. The maximal attainable sensitivity of the competitive assay is now $\epsilon/K$ where $\epsilon$ is the combined relative error due to experimental factors. Let us assume, for instance, that the experimental error is of the order of 1%; the maximal attainable sensitivity then, using an antibody with an affinity constant as high as possible, for instance, $10^{12}$ l/mol, is of the order of 0.01 picomol/l. The sensitivity definition also demonstrates that unless the experimental error can be almost completely eliminated (<0.1%), there is no sensitivity advantage to be gained in using a label with extremely high specific activity.

Likewise, the factors affecting the sensitivity of the non-competitive are the following:

a) the relative error of the signal strength ($\alpha$) when the analyte is omitted, i.e., the error due to non-specific binding of the labelled antibody (bioaffinity reactant)

b) the relative amount of non-specifically bound labelled antibody (k), and c) the affinity constant (K) of the antibody The sensitivity of the non-competitive assay is then $k/K \times \alpha$. The sensitivity of both competitive and non-competitive assay is inversely related to the affinity constant of the antibody used, but the non-competitive assay is affected by the relative error due to, on the one hand, non-specific binding of the labelled antibody and on the other hand, the relative binding of the labelled antibody, both of which could be assigned, for instance, a value of 1%. The maximal sensitivity of the non-competitive assay is then 0.0001×1/K or 0.1 fmol/l, if the affinity constant of the antibody used is $10^{12}$ l/mol, which is usually considered to be the highest possible value. In a non-competitive assay it is advisable to consider the specific activity of the label, because it affects factors a) and b), and offers a possibility to improve the sensitivity of the assay.

In assays based on bioaffinity reactions factors structurally limiting the sensitivity of various determinations must also be considered; this is also essential as regards the present invention, because measurements will be taken from individual microparticles with extremely small amounts of analytes present.

SUMMARY OF THE INVENTION

This invention relates to a biospecific assay method, in which method microparticles coated with the bioaffinity reactant A binding the analyte to be assayed; the sample to be analysed, and the labelled bioaffinity reactant B are mixed. After the binding reaction the signal strength from the labelled bioaffinity reactant B bound to the microparticles is quantitated for the determination of the analyte concentration of the sample. According to the present invention such an amount of sample and microparticles is used in the assay that after binding of the analyte of the sample to the said amount of microparticles, each individual microparticle will emit such a signal strength as to allow the measurement of the analyte concentration in the sample over the whole range of typical analyte concentrations, and the signal strength from each microparticle will be measured separately.

DETAILED DESCRIPTION OF THE INVENTION

Figure 1:
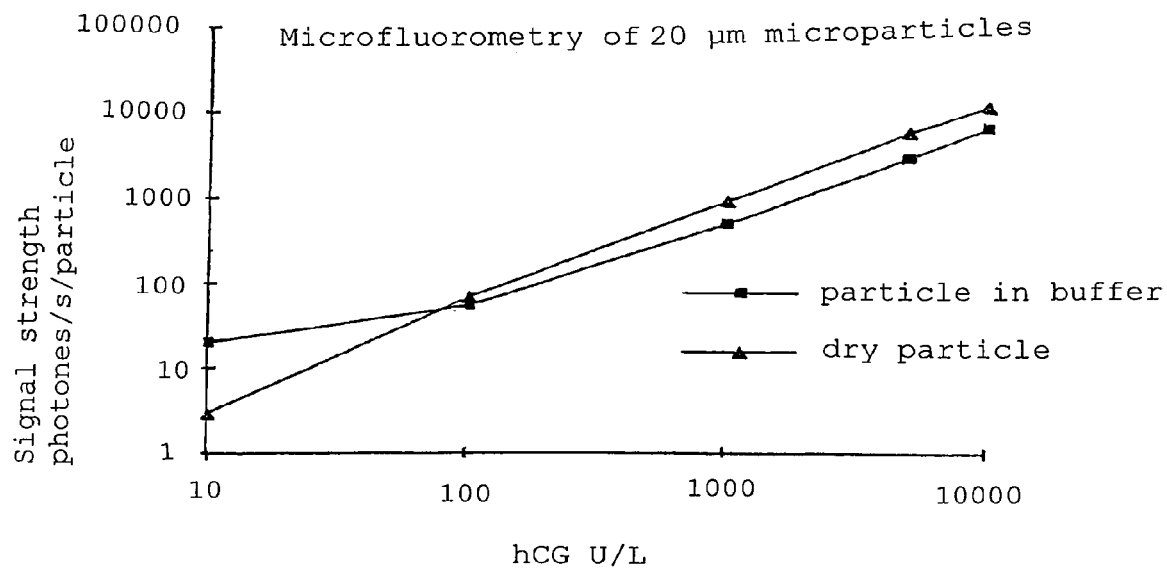
FIG. 1 shows a calibration curve for hCG construed by measuring individual microparticles by time-resolved microfluorometry

The present invention allows the assay of the analyte in the sample at a minimal analyte concentration and in a minimal volume by selecting such an amount of microparticles that allows the measurement of the analyte bound to the surface of an individual microparticle, by the sensitive label technology used. The biospecific reaction may be an immunoassay, a nucleic acid hybridization assay, a ligand-lectin assay or a ligand-receptor assay. The bioaffinity reaction may be advantageously performed on a microparticle having a diameter of less than 1 mm. The analyte concentration on the surface of the microparticle is determined by means of the labelled bioaffinity reactant B, the label being one emitting fluorescence, time-resolved fluorescence, chemiluminescence or bioluminescence. The present invention allows the measurement of both the highest and the lowest concentrations of analyte from individual microparticles. The sensitivity of the assay and the measurement range are controlled by the amount of microparticles used in the assay.

The present invention may be applied to many types of biospecific affinity reactions, although the most commonly used is the immunochemical reaction. This is why the present invention is predominantly described as a immunochemical assay. The relevant biospecific affinity reactions (immunoreactions) are either competitive or non-competitive. Both immunoassay principles are commonly known. The factors affecting the sensitivity of the said immunoassay methods are known and the optimal sensitivity of the assays can be calculated. The highest attainable sensitivity in the competitive assay is about 10 fmol/l. The sensitivity cannot be improved by increasing the specific activity of the label used. Sensitivity can be improved to a certain degree by using a minimal antibody concentration. In the competitive assay the signal strength from the label to be measured is inversely related to the concentration of the sample (analyte) to be assayed.

The highest possible sensitivity attainable in the non-competitive assay is about 0.1–0.01 fmol/l. The sensitivity may be enhanced if a label with a very high specific activity is available. The sensitivity can be improved up to a certain limit by using the highest possible concentration of labelled antibody if the background of the assay (non-specific binding to the surface) remains low. In the non-competitive assay the signal strength from the label to be measured is directly related to the concentration of the sample (analyte) to be assayed.

In the competitive immunoassay the assumption may be made that the measuring range of the analyte to be assayed is typically 100-fold, i.e., so wide that the ratio of the highest to the lowest measured value is 100. In the competitive assay the lowest concentration gives the strongest signal and the highest concentration gives the weakest signal. In the competitive assay based on the use of microparticles, in which the measurement is taken from individual particles, one must be able to measure the signal strengths from both the lowest and the highest concentration. If we assume a measuring range of 1–0.01 pmol/l for the sample to be assayed, then a concentration of 0.01 pmol/l corresponds to the strongest signal, and 1 pmol/l to the the weakest signal, respectively. The concentration of the analyte of the example is 1–0.01 attomol/μl which means that when using a sample volume of 1 μl (1–0.01 attomol of analyte to be assayed) one must be able to measure, from a single microparticle, both the highest (0.01 attomol of sample) and the lowest (1 attomol of sample) signal strength. This means that when the concentration of the competing analyte is low, the highest possible number of analyte, i.e. bioaffinity reactant molecules will specifically bind to the surface of a single microparticle coated with a specific antibody, i.e. a second bioaffinity reactant. The lowest analyte concentration means that a sample volume of 1 μl contains approximately 6,000 molecules of the analyte to be assayed, while the highest concentration corresponds to approximately 600,000 molecules in a microlitre, respectively. It is typical of the competitive assay that the signal strength decreases from about 100% to about 5–25% with increasing analyte concentration. The amount of the microparticles and of the analyte-specific antibody coated onto them will be adjusted to a minimal sample volume in order to allow a replacement (of labelled analyte by the analyte to be assayed) of 75–95% at the highest sample concentration. This still allows the remaining signal strength to be reproducibly measured, by the label technology used, from the surface of individual microparticles, and at the same time, the signal strength (due to the specific binding of labelled analyte to the coated microparticle) corresponding to the lowest analyte concentration will not exceed the binding capacity of individual particles. The measuring range is adjusted for different assays by altering the amounts of the microparticles and antibodies used in the assay method in such a manner that measurements can always be taken from individual microparticles.

The sensitivity of the non-competitive immunoassay is, at best, 0.01–0.1 fmol/l, and the measuring range is typically more than 100-fold, i.e. the ratio of the highest to the lowest measurement value is greater than 100. The signal strength measured in the assay is directly related to the concentration of the analyte to be assayed. For a required sensitivity of 0.01 pmol/l for the analyte to be assayed, and assuming a measuring range of 1,000-fold, a sample volume of 1 µl will contain 0.01–10 attomol of the analyte to be assayed. If the sensitivity of the label technology is about 6,000 molecules per one microparticle, and with a signal strength directly related to the concentration of the analyte, it is possible for one microparticle to bind the analyte contained in 1 µl, and the amount of the analyte can be measured. The amount of microparticles used in the assay can be increased without changing the sample volume, if the sensitivity of the label techonology is better or if a greater number of labelled molecules are linked to the labelled analyte-specific antibody (bioaffinity reactant). Accordingly, if the sensitivity of the label technology is lower, the sensitivity of the assay will decrease or the amount of analyte required on the surface of a single microparticle must come from a larger sample volume, which however limits the measurement range. The amount of the microparticles used in the assay, coated with the analyte-specific antibody or bioaffinity reactant as well as the amount of the analyte per microparticle will be adjusted so that a minimal concentration and volume of the analyte will contain enough analyte for binding to the surface of individual microparticles, and enough for measurement from individual microparticles by means of a labelled specific antibody (labelled bioaffinity reactant) and with the sensitive label technology used. The measurement range required and the sensitivity of the measurement will be controlled by adjusting the amount of microparticles used in the assay and by adjusting sample volume, if needed.

Other specific bioaffinity assays such as nucleic acid hybridization assays, ligand-lectin assays and ligand-receptor assays are comparable to the immunoassay methods described above.

Individual microparticles can be assayed with e.g. a flow cytometer, time-resolved microscope or time-resolved microfluorometer or with other measuring instruments based on the use of time-resolved technology (U.S. Pat. No. 5,028,545; Seveus L et al., Cytometry 13: 329–338 (1992).

Microparticles may also eventually be used in multiparameter assays, in which several analytes are simultaneously assayed in the same sample volume. In the multiparameter assay a mixture of microparticles is used, in which the particles assaying for different analytes are coated with analyte-specific bioaffinity reactants. When the measurement is taken the analyte-specific microparticle categories are identified on the basis of e.g. size, fluorescence, time-resolved fluorescence, chemiluminescence or biolumines- cence. The multiparameter assays using microparticles, based on a bioaffinity reaction are performed according to the present method. In the case of several analytes being assayed simultaneously the amount of the analyte-specific microparticles used in the assay is adjusted according to analyte following the above principles.

The present invention will also be illustrated by the following non-restrictive examples.

EXAMPLE 1

Quantitation of label (fluorescent Eu chelate) per microparticle and immunoassay measurement from individual microparticles using as a model the non-competitive hCG assay and measurement based on time-resolved fluorescence.

The hCG (hCG=human chorionic gonadotrophin) assay has been performed as a non-competitive immunoassay with a specific monoclonal antibody against the β subunit being biotinylated and bound to 20 µm microparticles coated with streptavidin. The labelled bioaffinity reactant has been a monoclonal antibody labelled with a fluorescent Eu chelate, specifically recognizing the α subunit of hCG. The immunoassay has been performed in one step, during which the antibody-coated microparticles, the hCG calibration standard (2–10,000 U/l, where U/l=unit/l) and the labelled antibody are all present simultaneously. After the immunoassay the number of microparticles has been checked by counting, and the Eu concentration has been determined from the known microparticle amount by using the DELFIA assay solution, which then allows the calculation of the amount of Eu molecules per microparticle. In addition individual microparticles have been measured by time-resolved microfluorometry which allows the measurement of the concentration per microparticle of the hCG-specific antibody labelled with fluorescent Eu chelate. The hCG assay presented as an example has not been completely optimized.

Results: Table 1 shows the results of the hCG assay when using 20 µm microparticles. In these assay conditions the lowest hCG concentration resulted in about 5,000 Eu molecules per microparticle, the variation within the experiment still being wide. In addition the measuring range is at least 1,000-fold. FIG. 1 shows a calibration curve for hCG construed by measuring individual microparticles by time-resolved microfluorometry.

EXAMPLE 2

The effect of the amount of microparticles coated with antibody (bioaffinity reactant) on the sensitivity of the assay using as a model the non-competitive hCG immunoassay and the measurement of individual microparticles with a microfluorometer, based on time-resolved fluorescence.

The immunoassay of hCG was performed according to the preceding example. A total volume of 20 µl, three concentrations of calibration standard (0, 250, and 2,500 U/l) and three different amounts of microparticles were used in the assay. After the immunoreaction individual microparticles were measured by time-resolved microfluorometry.

Figure 2:
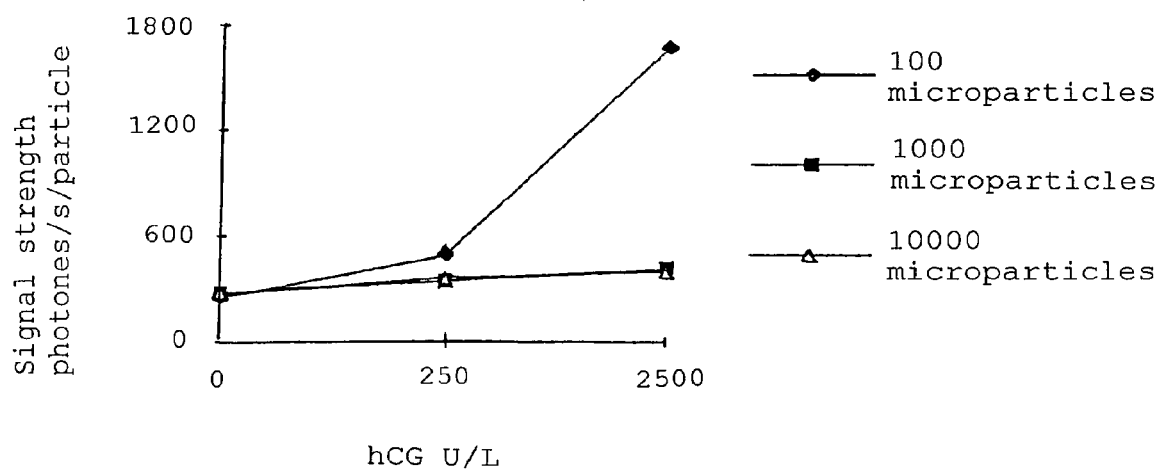
FIG. 2 shows the signal strength versus analyte concentrations for different amounts of microparticles (measured from individual microparticles)

Results: Table 2 and FIG. 2 show the effect of the amount of microparticles on the signal strength (photons/s/particle) measured from individual microparticles; with a smaller amount of microparticles the hCG (analyte) in the sample will be bound in a higher concentration onto the surface of individual microparticles; the sensitivity of the assay and the measurement range may be controlled, if needed, by the amount of the microparticles and the sample volume, so as to allow measurement from individual microparticles. The reproducibility of the assay can be improved by measuring a greater number of individual microparticles.

EXAMPLE 3

The effect of the amount of microparticles on nucleic acid hybridization reaction using two different concentrations of target nucleic acid.

The microparticles, of a diameter of 20 μm, were coated with streptavidin and used in a hybridization assay where the target was biotin-labelled synthetic oligonucleotide and the probe a synthetic oligonucleotide labelled with a fluorescent Eu chelate. The experiment was performed using two different amounts of target oligonucleotide ($10^9$ and $10^{10}$ molecules). The total assay volume was 20 μl and 2.0 ng of probe labelled with the fluorescent Eu chelate was used in each assay. The amount of microparticles used per experiment varied from 10–10,000 for each target oligonucleotide concentration. After the hybridization reaction the Eu concentration was measured from the surface of the microparticles by time-resolved microfluorometry.

Figure 3:
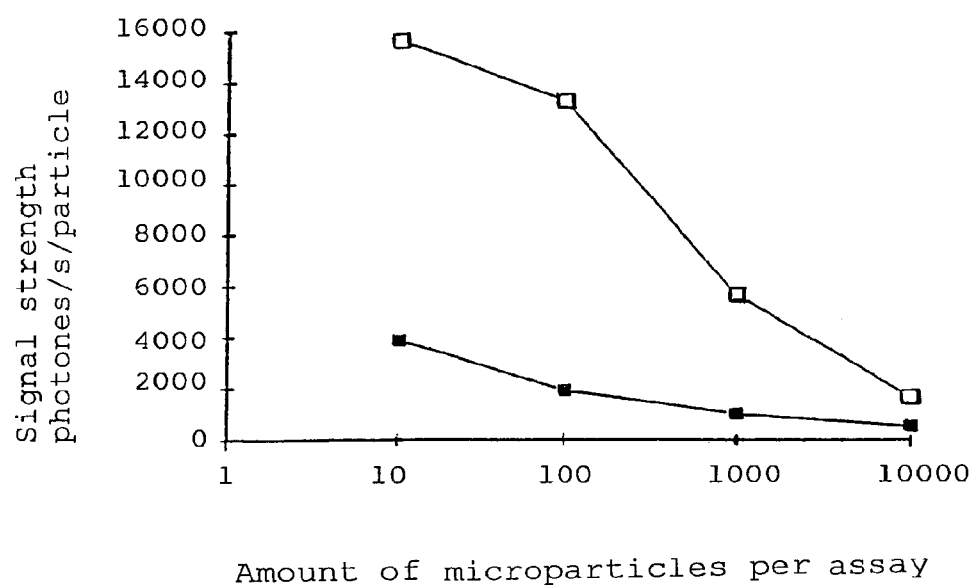
FIG. 3 shows the signal strength versus amount of microparticles per assay for two different amounts of analyte DNA present in the reaction (measured from individual microparticles). The curve indicated by closed squares represents $10^9$ molecules per reaction and the curve indicated by open squares represents $10^{10}$ molecules per reaction.

Results: Table 3 and FIG. 3 show the effect of the amount of microparticles on the signal strength measured from individual microparticles; with a smaller amount of microparticles the amount of the target oligonucleotide in the sample will bind in higher concentration onto the surface of individual microparticles; again the sensitivity of the assay and the measurement range may be controlled, if needed, by the amount of microparticles used and by the sample volume so as to allow measurement from individual microparticles.

A specialist in the field will appreciate that the different applications of the said invention may vary within the scope of the claims. It will be appreciated that the methods of the present invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

TABLE 2

Effect of the amount of microparticles on the signal strength

| hCG U/l | particles | signal strength photons/s/part. | CV % |
|---|---|---|---|
| 0 | 100 | 252 | 6.5 |
| 250 | 100 | 490 | 26.15 |
| 2500 | 100 | 1671 | 23.1 |
| 0 | 1000 | 277 | 10.39 |
| 250 | 1000 | 345 | 15.76 |
| 2500 | 1000 | 418 | 19.98 |
| 0 | 10000 | 278 | 7.05 |
| 250 | 10000 | 366 | 23.34 |
| 2500 | 10000 | 401 | 38.5 |

Total assay volume 20 μl, of which standard=5 μl. Size of microparticles 20 μm. Microfluorometry, laser excitation, attenuation 1:100.

TABLE 3

| amount of particles | amount of analyte molecules | signal strength photons/s/part. | CV % |
|---|---|---|---|
| 10000 | $10^8$ | 497 | 34 |
| 1000 | " | 1005 | 48 |
| 100 | " | 1885 | 22 |
| 10 | " | 3852 | 24 |
| no analyte/100 | | 1358 | 40 |
| 10000 | $10^{10}$ | 1622 | 31 |
| 1000 | " | 5613 | 25 |
| 100 | " | 13236 | 33 |
| 10 | " | 15594 | 45 |
| no analyte/100 | | 1887 | 43 |

The invention claimed is:

1. In a biospecific assay method comprising
reacting microparticles coated with a bioaffinity reactant A which specifically binds at least one analyte to be assayed, a sample to be analyzed, and a labelled bioaffinity reactant B to cause said analyte and said

TABLE 1

Calculated Eu amounts in hCG-standards using 20 μm particles. Great assay amount.

| hCG U/l | signal strength photons/s | particles | Eu fmol | Eu fmol/cm² | Eu mol/part. | Eu molecules/ particle | average | % CV |
|---|---|---|---|---|---|---|---|---|
| 2 | 118 | 9624 | 0.082 | 0.678 | $8.52 \times 10^{-21}$ | 5130 | | |
| | <0 | 10451 | | | | | | |
| | <0 | 7444 | | | | | 5130 | |
| 10 | 130 | 7970 | 0.09 | 0.899 | $1.13 \times 10^{-20}$ | 6805 | | |
| | <0 | 6917 | | | | | | |
| | 306 | 6090 | 0.212 | 2.77 | $3.48 \times 10^{-20}$ | 20957 | 13881 | 72.09 |
| 100 | 817 | 7293 | 0.566 | 6.176 | $7.76 \times 10^{-20}$ | 46732 | | |
| | 869 | 6165 | 0.603 | 7.783 | $9.78 \times 10^{-20}$ | 58897 | | |
| | 1030 | 8195 | 0.714 | 6.933 | $1.17 \times 10^{-19}$ | 70459 | 58696 | 20.21 |
| 1000 | 12955 | 7293 | 9.98 | 97.99 | $1.23 \times 10^{-18}$ | 740727 | | |
| | 13142 | 9624 | 9.11 | 75.33 | $9.47 \times 10^{-19}$ | 570299 | | |
| | 11474 | 8797 | 7.96 | 72.01 | $9.05 \times 10^{-19}$ | 545006 | 618677 | 17.21 |
| 5000 | 78247 | 5940 | 54.26 | 726.92 | $9.14 \times 10^{-18}$ | 5504263 | | |
| | 71234 | 7820 | 49.4 | 502.7 | $6.32 \times 10^{-18}$ | 3806011 | | |
| | 70166 | 7368 | 48.66 | 525.55 | $6.60 \times 10^{-18}$ | 3974632 | 4428302 | 21.13 |
| 10000 | 146072 | 6090 | 101.29 | 1323.55 | $1.66 \times 10^{-17}$ | 9996802 | | |
| | 112916 | 7368 | 78.3 | 845.67 | $1.06 \times 10^{-17}$ | 3683500 | | |
| | 113853 | 6541 | 78.95 | 960.5 | $1.21 \times 10^{-17}$ | 7286826 | 6989043 | 45.32 |

CV = coefficient of variation labelled bioaffinity reactant B to specifically bind to said microparticles via the bioaffinity reactant A; and measuring signal strength from labelled bioaffinity reactant B bound to the microparticles to determine the analyte concentration in the sample, the improvement comprising:

contacting a predetermined amount of said sample, a predetermined number of uniformly sized microparticles coated with said bioaffinity reactant A and said labelled bioaffinity reactant B labelled with a luminescent label such that, after the specific binding of the analyte in the sample to said predetermined number of uniformly sized microparticles, each individual microparticle emits a signal strength that corresponds to the analyte concentration in the sample, and measuring the signal strength from an individual microparticle using a measuring means capable of reading the luminescence from an individual microparticle, and determining the analyte concentration in the sample by comparing said signal strength measured from said individual microparticle with a standardization curve, wherein said standardization curve is a mean of the signal strength of said predetermined number of uniformly sized microparticles.

2. The assay method according to claim 1, wherein the assay comprises a non-competitive immunoassay, in which the labelled bioaffinity reactant B comprises an antibody which specifically binds to the analyte.

3. The assay method according to claim 1, wherein the assay comprises a nucleic acid hybridization assay, in which the labelled bioaffinity reactant B comprises a nucleic acid probe which specifically hybridizes with the analyte.

4. The assay method according to claim 1, wherein the microparticles used comprise a mixture of microparticles recognizing different analytes.

5. The assay method according to claim 1, wherein said luminescent label is selected from the group consisting of labels emitting fluorescence, time-resolved fluorescence, chemiluminescence and bioluminescence.

6. The assay method according to claim 1, wherein the assay comprises a competitive immunoassay, in which the labelled bioaffinity reactant B comprises an antigen, and the bioaffinity reactant A is an antibody for whose binding sites the labelled antigen and the analyte compete.

7. The assay method according to claim 6, wherein the amount of said predetermined number of uniformly sized microparticles coated with the antibody A is adjusted so that the lowest analyte concentration will result in the strongest signal.

* * * * *